United States Patent
Dadiani et al.

(10) Patent No.: US 10,810,740 B2
(45) Date of Patent: Oct. 20, 2020

(54) SYSTEM AND METHOD FOR AUTOMATED CHARACTERIZATION OF SOLID TUMORS USING MEDICAL IMAGING

(71) Applicant: TEL HASHOMER MEDICAL RESEARCH INFRASTRUCTURE AND SERVICES LTD., Ramat-Gan (IL)

(72) Inventors: Maya Dadiani, Rehovot (IL); Arnaldo Mayer, Herzliya (IL); Miriam Sklair-Levy, Mevasseret-Zion (IL)

(73) Assignee: TEL HASHOMER MEDICAL RESEARCH INFRASTRUCTURE AND SERVICES LTD., Ramat-Gan (IL)

( * ) Notice: Subject to any disclaimer, the term of this patent is extended or adjusted under 35 U.S.C. 154(b) by 101 days.

(21) Appl. No.: 16/317,831

(22) PCT Filed: Jul. 19, 2017

(86) PCT No.: PCT/IL2017/050810
§ 371 (c)(1),
(2) Date: Jan. 15, 2019

(87) PCT Pub. No.: WO2018/015953
PCT Pub. Date: Jan. 25, 2018

(65) Prior Publication Data
US 2020/0167926 A1    May 28, 2020

Related U.S. Application Data

(60) Provisional application No. 62/364,392, filed on Jul. 20, 2016.

(51) Int. Cl.
*G06K 9/00* (2006.01)
*A61B 5/05* (2006.01)
(Continued)

(52) U.S. Cl.
CPC ............ *G06T 7/0016* (2013.01); *G06T 5/002* (2013.01); *G06T 7/38* (2017.01); *G06T 7/564* (2017.01);
(Continued)

(58) Field of Classification Search
USPC ........ 382/100, 103, 106–107, 128–134, 155, 382/173, 181, 199, 224, 254, 274, 276,
(Continued)

(56) References Cited

U.S. PATENT DOCUMENTS

| | | | |
|---|---|---|---|
| 8,200,312 B2 * | 6/2012 | Degani | A61B 5/03 600/420 |
| 2010/0080757 A1 * | 4/2010 | Haaga | A61B 6/481 424/9.3 |

(Continued)

OTHER PUBLICATIONS

Cancer Res., vol. 72, No. 19, pp. 4899-4908, 2012, T. Hompland, C. Ellingsen, K. M. Ovrebo, and E. K. Rofstad, "Interstitial fluid pressure and associated lymph node metastasis revealed in tumors by dynamic contrast-enhanced MRI." Published Oct. 2012.

*Primary Examiner* — Seyed H Azarian
(74) *Attorney, Agent, or Firm* — Naomi S. Rosenman-Helfand

(57) ABSTRACT

A system and method for automated characterization of solid tumors using medical imaging. The system comprises an interface that is configured to acquire data from medical imaging devices, one or more processors, and an outputting device that reports the characterization of said solid tumor. The method of automated characterization, which is implemented by the system, acquires a sequence of images from the medical imager using a Dynamic Contrast Enhanced (DCE) imaging protocol, performs image registration, detects the contour of the solid tumor, and dividing the contours to segments. For each segment, the method calculating a displacement of the contrast material, fitting the
(Continued)

displacement to a flow model and extracting an estimation of the interstitial fluid velocity. The estimated interstitial fluid velocity of the segments provide characterization of the solid tumor and includes an assessment of the tumor interstitial fluid pressure, the tumor drug delivery efficiency, and the tumor prognostic or metastasis risk.

19 Claims, 4 Drawing Sheets

(51) Int. Cl.
*G06T 7/00* (2017.01)
*G06T 7/564* (2017.01)
*G06T 7/38* (2017.01)
*G16H 30/20* (2018.01)
*G16H 50/20* (2018.01)
*G16H 30/40* (2018.01)
*G06T 5/00* (2006.01)

(52) U.S. Cl.
CPC ............. *G16H 30/20* (2018.01); *G16H 30/40* (2018.01); *G16H 50/20* (2018.01); *G06T 2207/10096* (2013.01); *G06T 2207/20084* (2013.01); *G06T 2207/20116* (2013.01); *G06T 2207/30068* (2013.01); *G06T 2207/30096* (2013.01)

(58) Field of Classification Search
USPC .......... 382/291, 305; 424/9.3; 600/420, 419; 378/4, 21
See application file for complete search history.

(56) References Cited

U.S. PATENT DOCUMENTS

2013/0329973 A1* 12/2013 Cao ...................... A61B 5/0033
  382/128
2017/0071496 A1* 3/2017 Gillies ................. A61B 5/0263
2017/0243349 A1* 8/2017 Hou ......................... G06T 7/73
2019/0180139 A1* 6/2019 Zach .................... G06K 9/6202

\* cited by examiner

SYSTEM AND METHOD FOR AUTOMATED CHARACTERIZATION OF SOLID TUMORS USING MEDICAL IMAGING

FIELD OF THE INVENTION

The invention generally relates to imaging technology for medical diagnostic purposes. More specifically, the invention describes a system and method for physical characterization of solid tumors, using standard MRI scanners. The invention provides knowledge on the interstitial fluid velocity, at the site of the scanned tissue, which can be used to select a treatment option for detected solid tumors.

BACKGROUND OF THE INVENTION

One major factor contributing to resistance of tumors to therapy is high Interstitial Fluid Pressure (IFP) in the area surrounding a solid tumor, as high IFP prevents efficient drug delivery. IFP is known to have a major effect on drug uptake by controlling the flow of blood-borne chemotherapeutic agents into the tumor interstitium, the tissue space surrounding the cells. It is well established that most solid tumors demonstrate high pressure in the tumor interstitium. Elevated IFP in tumors is a consequence of abnormal tumor vasculature, high vascular permeability and absence of functional lymphatic drainage. The fluid pressure is elevated in tumors except at the margin, where it steeply drops.

The pressure gradient between the tumor and the normal tissue causes fluid to leak out of the tumor. This high peritumoral Interstitial Fluid flow Velocity (IFV) facilitates outflow of tumor-generated growth factors and metastatic tumor cells, and results in poor delivery of systemically administered therapies to tumors, such as conventional cytotoxic agents and monoclonal antibodies.

High IFP has been shown to be associated with metastasis and with poor clinical outcome. Thus, an effective assessment of the IFP or IFV in patients, could be used as a predictor of their future resistance to therapy. Estimating the presence of such a potential barrier to drug delivery, can prevent ineffective treatments and improve the treatment plan.

To date, measurement of IFP has been performed by invasive needle insertion. This method is inaccurate and painful, and thus is not suitable for routine assessment of solid tumors.

Attempts were made to non-invasively assess the IFP levels, in pre-clinical and clinical studies. However, prior art methods were dependent on MRI acquisition sequences, and therefore not repeatable between different MRI machines. Other methods required complicated analysis based on pharmacokinetic models, or were not applicable to routine MRI examinations.

For instance, U.S. Pat. No. 8,200,312 to Degani et al., utilized dynamic contrast-enhanced MRI (DCE-MRI) to assess IFP. The '312 method required slow infusion of the contrast material until a "steady state" was achieved (see FIGS. 1, 2), necessitating over two hours of MRI scanning time (infusion time), which is impractical in a routine hospital setting, such a busy radiology department. The '312 additionally depends on the parameters which may vary from one hospital setting to another, such as the MRI acquisition protocol, and the pharmacokinetic parameters, so that the results are not comparable between different institutions.

In another attempt to non-invasively determine the IFV, a clinical study to Hompland et al., utilized a physical model to assess the interstitial fluid flow velocity (IFV) in the peritumoral tissue surrounding several types of tumors (Cancer Res., vol. 72, no. 19, pp. 4899-4908, 2012, T. Hompland, C. Ellingsen, K. M. Ovrebo, and E. K. Rofstad, "Interstitial fluid pressure and associated lymph node metastasis revealed in tumors by dynamic contrast-enhanced MRI."). The evaluated velocity was correlated to the standard (invasive needle insertion) measurement of IFP. Disappointingly, the method required a manual analysis to identify several points along the tumor rim images of each patient, which does not provide sufficient data for a robust method. Additionally, such manual activity is too time-consuming to be feasible for use as a routine clinical method.

It would be advantageous if an automatic non-invasive test could be developed for assessment of the IFV in mammalian tissues, which would not require excessive time and efforts from medical staff or from the patient.

It is an object of the invention to provide a clinically-reliable and non-invasive method to measure IFV as an assessment of the IFP level in mammalian tissue, and thus predict the efficiency of drug uptake.

Patients found to have a solid tumor and an elevated IFV, could be treated accordingly, for example by using targeted therapies to reduce tumor hypertension and increase the efficiency of drug delivery. Such targeted therapies have not been tested to date on patients, due to the lack of a routine method to assess the IFP.

The method should be automatic, and should not require extra effort from the radiologist reviewing the images or from other medical personnel.

These and other features and advantages will become more apparent from the Detailed Description that follows.

SUMMARY OF THE INVENTION

The present invention describes automatic assessment of the peritumoral IFV, using images taken during routine Dynamic Contrast-Enhanced (DCE) imaging examinations of mammalian tissue.

In a general overview, the invention provides novel image processing techniques, to track the tumor rim (hereinafter, for the sake of matching the terminology with the terminology used in the field of image processing, will be referred as tumor contour), calculate the fluid flow velocity and map the fluid flow throughout the peritumoral regions. The invention utilizes standard DCE protocols, and is performed automatically using the software of the invention, without any added interventions from the radiologist other than the routinely performed identification of the tumor borders. The invention enables analysis of any available image datasets, and is not limited to a specific MRI protocol or other imaging protocol (which may vary from one hospital to another).

Dynamic Contrast Enhanced imaging describes acquisition of baseline image(s) without contrast enhancement ("pre-contrast"), followed by a series of images acquired over time after an intravenous bolus of conventional contrast material ("post-contrast"). The presence of CA (contrast agent) within blood vessels and tissues affects measured X-ray attenuation on CT in a linear fashion and the calculated signal intensity on MRI in a non-linear manner Thus, the temporal changes in contrast enhancement effectively provide a time-concentration curve, which can be analyzed to quantify a range of physiological parameters that indicate the functional status of the vascular system within tumors and adjacent tissues. During the first-pass of the CA through the circulation (typically 45-60 s after injection), CA is predominantly intravascular allowing evaluation of perfusion (i.e. blood flow per unit volume or mass of tissue), relative blood volume (rBV) and mean transit time. During the subsequent 2-10 min, there is increasing passage of CA into the extravascular space, and imaging during this delayed phase enables measurement of vascular permeability and relative extravascular volume.

According to an aspect of some embodiments of the present invention there is provided a method for automated characterization of solid tumors in mammalian tissue, using medical imaging, the method comprising: (a) acquiring a sequence of images of mammalian tissue, captured with a medical imager using a Dynamic Contrast Enhanced (DCE) imaging protocol; (b) performing image registration of the sequence of images to align the sequence of images and compensate for at least one of the following: patient movements, respiration movement, and gravity effects; (c) if a solid tumor is present, detecting a contour of the solid tumor in each one of the post contrast images, among the sequence of images; (d) dividing the contours to segments, and matching segments that are related to different images, in the sequence of images; (e) calculating a displacement of the contrast material of the DCE protocol between each of the matched segments; (f) fitting the displacements to a fluid flow model, and extracting for each segment, an estimation of the interstitial fluid velocity; (g) conditioned upon one or more of the estimations of the interstitial fluid velocity of the segments, calculating and reporting a characterization of the solid tumor, wherein the characterization comprises an assessment for at least one of or any combination of: the tumor and/or peri-tumor interstitial fluid velocity, the tumor interstitial fluid pressure, the tumor drug delivery efficiency, or the tumor prognostic or metastasis risk.

According to some embodiments of the invention, in step (g) only a portion of the segment interstitial fluid velocity estimations are used in calculating the solid tumor characterization.

According to some embodiments of the invention, step (f) is further comprises an extracting, for each segment, an estimation of attenuation coefficient of the interstitial fluid flow model;

According to some embodiments of the invention, in step (c) the contour is detected using a Distance Regularized Level Set Evolution (DRLSE) algorithm.

According to some embodiments of the invention, step (c) comprises an initial contour guess, either manually marked by a radiologist, or automatically detected by at least on of or any combination of the following algorithms: (1) K-means, (2) Mean-shift, (3) Expectation-Maximization fitting, or (4) edge detection.

According to some embodiments of the invention, step (c) further comprises smoothing the contour.

According to some embodiments of the invention, calculating the displacements in step (e) is based on Hausdorff distance between the segments.

According to some embodiments of the invention, fitting the displacements to a fluid flow model in step (f) is performed using a non-linear least squares regression analysis.

According to some embodiments of the invention, step (e) and step (f) further comprise preparing a spatial-temporal data vector of the segment, inputting the spatial-temporal data vector into an artificial neural network that is pre-trained to provide an estimation of the interstitial fluid velocity of the segment.

According to some embodiments of the invention, the method further comprises providing maps of interstitial fluid velocities at the contour of the solid tumor.

According to some embodiments of the invention, the medical imager is a magnetic resonance imager (MRI).

According to some embodiments of the invention, the medical imager is an X-ray tomography imager.

According to some embodiments of the invention, the medical imager is at least one of or any combination of: (a) X-ray tomography imager, (b) magnetic resonance imager (MRI), (c) Positron emission tomography (PET), (d) Single-photon emission computed tomography (SPECT), and (e) Ultrasound imager.

According to some embodiments of the invention, the segments in step (d) are extracted from a single image slice, wherein the tumor is seen largest in this slice.

According to some embodiments of the invention, the segments in step (d) are extracted from a plurality of image slices.

According to some embodiments of the invention, the segments in step (d) are two-dimensional (2D) surfaces patches extracted from the images.

According to some embodiments of the invention, steps (e) and step (f) are replaced with the steps of preparing of a spatial-temporal data vector of the segment, and inputting the spatial-temporal data vector into an artificial neural network that is pre-trained to provide an estimation of the interstitial fluid velocity of the segment.

According to an aspect of some embodiments of the present invention there is provided a computing system for automated characterization of solid tumors, the computing system comprising:

i. an interface, wherein the interface is configured to acquire data from medical imaging devices;
ii. one or more processors, wherein the processors are configured to perform the following:
  (a) acquire a sequence of images from a medical imager using a Dynamic Contrast Enhanced (DCE) imaging protocol;
  (b) perform image registration of the sequence of images to align the sequence of images and compensate for at least one of the following: patient movements, respiration movement, and gravity effects;
  (c) if a solid tumor is present, detect a contour of the solid tumor in each one of the post contrast images, among the sequence of images;
  (d) divide the contours to segments, and match segments that are related to different images, in the sequence of images;
  (e) calculate a displacement of the contrast material of the DCE protocol between each of the matched segments;
  (f) fit the displacements to a fluid flow model, and extract for each segment, an estimation of the interstitial fluid velocity;
  (g) conditioned upon one or more of the estimations of the interstitial fluid velocity of the segments, calculate and report a characterization of the solid tumor, wherein the characterization comprises an assessment for at least one of or any combination of:
    the tumor or peri-tumor interstitial fluid velocity,
    the tumor interstitial fluid pressure,
    the tumor drug delivery efficiency, or
    the tumor prognostic or metastasis risk; and
iii. an outputting device that reports the characterization of the solid tumor.

According to some embodiments of the invention, the acquired data is data from a magnetic resonance imager (MRI).

According to some embodiments of the invention, the acquired data is data from an X-ray tomography imager.

According to some embodiments of the invention, the acquired data is data from is at least on of or any combination of: (a) X-ray tomography imager, (b) magnetic resonance imager (MRI), (c) Positron emission tomography (PET), (d) Single-photon emission computed tomography (SPECT), (e) Ultrasound imager.

According to an aspect of some embodiments of the present invention there is provided a non-transitory computer readable medium storing a program causing a computer to execute the method of characterization of solid tumors described hereinabove.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

BRIEF DESCRIPTION OF THE DRAWINGS

The present invention is illustrated by way of example in the figures of the accompanying drawings, in which like references indicate similar elements and in which.

DETAILED DESCRIPTION OF THE INVENTION

Figure 1:
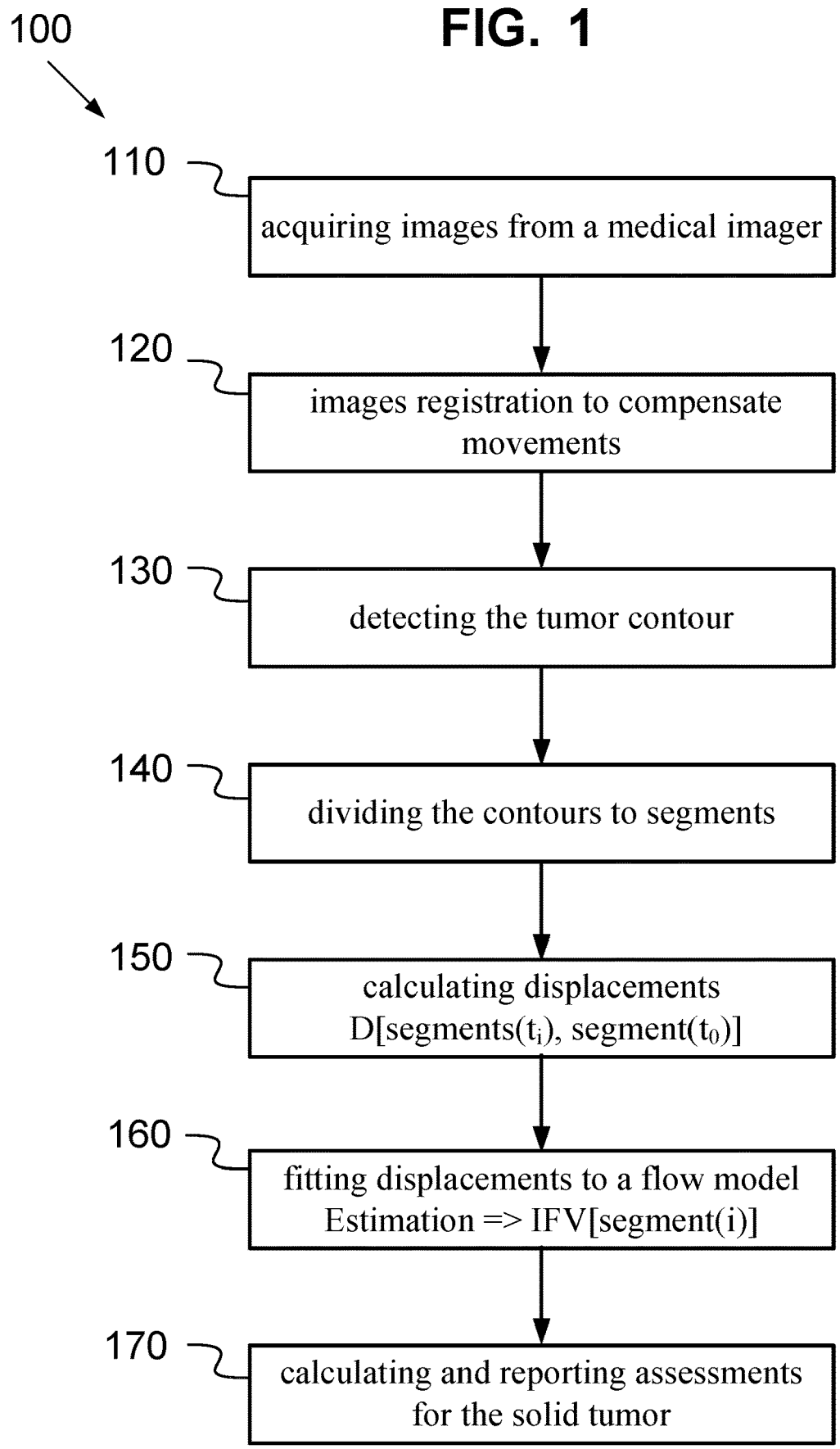
FIG. 1 is a flow chart of a method for assessment of Interstitial Fluid Pressure (IFP) of solid tumors from medical imaging data.

In the following detailed description, numerous specific details are set forth in order to provide a thorough understanding of the present invention. There is no intention to limit the invention to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

The present invention describes automatic assessment of the IFP or the peritumoral IFV, using images taken during routine dynamic contrast-enhanced MRI examinations of mammalian tissue. In a general overview, the invention provides novel image processing techniques, to track the tumor rim (hereinafter, for the sake of matching the terminology with the terminology used in the field of image processing, will be referred hereinafter as tumor contour), calculate the fluid flow velocity and map the fluid flow throughout the peritumoral regions. The invention utilizes standard contrast-enhanced MRI protocols, and is performed automatically using the software of the invention, without any added interventions from the radiologist other than the routinely performed identification of the tumor borders. The invention enables analysis of any available MRI image datasets, and is not limited to a specific MRI protocol (which may vary from one hospital to another).

Reference is now made to FIG. 1. FIG. 1 is a flow chart of a method for automated characterization of solid tumors using medical imaging. The method is based on medical imaging of the tumor using Dynamic Contrast Enhanced (DCE) imaging protocol. The term "Dynamic Contrast Enhanced (DCE) imaging protocol" refers herein to a medical imaging method where images are acquired dynamically after injection of a contrast material. As used herein, the term "pre-contrast image" means an image that acquired before the injection of the contrast material. As used herein, the term "post-contrast image" means an image that acquired after the injection of the contrast material. Generally, a sequence of post contrast images are taken to analyze the dynamics of the diffusion of the contrast material. Contrast material may be gadolinium, iodine, barium, saline solution or the like. The contrast material selected at least conditioned upon the type of imager and the type of tumor.

The method 100 sequentially performs steps 110 to step 170. Step 110 is acquiring a sequence of images from a medical imager in accordance with a Dynamic Contrast Enhanced (DCE) imaging protocol.

Step 120 is performing image registration of the sequence of images to align the sequence of images and compensate for one of or any combination of: a patient's movements, respiration movements, and gravity effects.

The alignment is performed if any misalignment between the images exists. The misalignments might be because of the movements of the patient between successive image taken, movement due to respiration, movements due to gravity forces during movements and the like.

The image registration can be performed using many known algorithms in the art. For example, the image registration may be performed by maximization of the normalized mutual information as disclosed by J. P. Pluim, J. B. Maintz, and M. A. Viergever, in a paper entitled "Image registration by maximization of combined mutual information and gradient information", published in IEEE Trans. Med. Imaging, vol. 19, no. 8, pp. 809-814, August 2000. The alignment processing must handle the significant intensity variations between consecutive images during post-contrast material injection time.

Step 130 is detecting a contour of the solid tumor in each post contrast images of the solid tumor. To emphasize the tumor and clarify the images, subtracted images are used: Subtracted images are post contrast images, containing only the difference from the pre-contrast image. There are many ways to detect the contour from an initial contour in each image in the sequence.

In an exemplary embodiment of the invention, the contour is detected using a Distance Regularized Level Set Evolution (DRLSE) algorithm, disclosed by C. Li, C. Xu, C. Gui, and M. D. Fox, in a paper entitled "Distance regularized level set evolution and its application to image segmentation", published in IEEE Trans. Image Process., vol. 19, no. 12, pp. 3243-3254, December 2010.

Optionally, to further improve the contour detection, a smoothing step is performed. Many type of smoothing tools may be used including applying variety of low pass filters. In an exemplary embodiment of the invention, edge-preserving anisotropic diffusion smoothing is performed.

In exemplary embodiment of the invention, an initial contour guess is used. The initial contour may be rough contour defined by markers added to one of the images by a radiologist. Alternatively, automatic edge filters may be used. Additionally or alternatively, lesion segmentation algorithms may be used based on intensity and/or texture features clustering by well-known K-means or Mean-shift algorithms or by Expectation-Maximization fitting of a Gaussian mixture-models. Segmentation algorithms based on Fully Convolutional neural networks may be used as well.

As used herein the term "contour" is a 1D curve or a 2D non-planar surface representing the boundary of the tumor in a 2D image or a 3D image respectively. The contour may include margins due to the diffusion of the contrast materials.

In exemplary embodiment of the invention, the contour used for segmentation is the contour generated from the image slice where the largest cross section of the tumor exist. Alternatively, the contours used for segmentation comprises contours from a plurality of slices. Yet another option, is to have contours generated from slicing, e.g. cross-sectioning, the tumor from different directions. In yet another exemplary embodiment, the contour is a 2D non-planar surface representing the boundary of the 3D tumor. In this case, the segments used in the calculations are 2D surface patches.

Step 140 is dividing the contours detected in the previous steps into segments. The segments that are related to different images in the sequence of images are matched to each other so any segment that is defined in the first post contrast image has a matching segments in every post contrast images.

The motivation to divide the contour to segments lies in the fact that estimating a displacement versus time of a single point (or single pixel/voxel) in the contour is very noisy and trying to estimate a displacement versus time of the full contour is a highly complex task since not all portions of the tumor exhibit the same displacement. In an exemplary embodiment of the invention the tumor contour is split into 500 segments. Alternatively, the number of segments the tumor contour is split to is in the range of 10 to 10,000. Preferably, each minimal segment contains at least 2 pixels in each direction.

Step 150 is calculating a displacement of each segment in all post contrast times in which images were taken. The displacement is calculated between two segments.

In an exemplary embodiment of the invention the segments are 1D planar curves. Alternatively, the segments are 2D surfaces patches.

There are many possible ways to calculate the distance or displacement between two curves or surfaces. In an exemplary embodiment of the invention, the displacement between the segments is calculated by the Hausdorff distance. The Hausdorff distance is the longest distance of all of the distances from a point in one segment to the closest point in the other segment. Alternatively, other distance measures such as averaging the distance to the closest point for all points in the earliest in time segment may be used.

Figure 2:
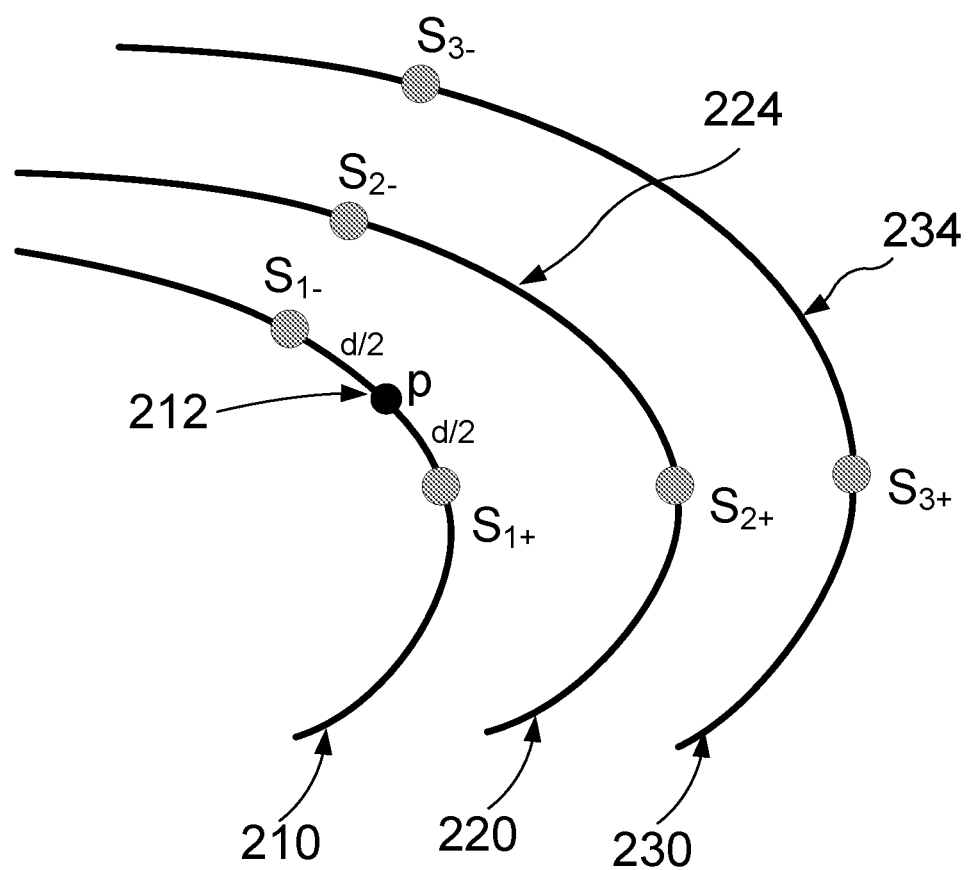
FIG. 2 is illustrates the principal of the segmenting, for contours detected in three post-contrast images.

Reference is now made to FIG. 2. FIG. 2 illustrates the principal of the segmenting, for contours detected in three post-contrast images. The figure illustrates three contours (for clarity only a partial view of the full contours is illustrated); contour 210 is the tumor contour in the first post contrast image, contour 220 is the tumor contour in the second post contrast image, and contour 230 is the tumor contour in the third post contrast image. Point p 212 on contour 210 is a selected point on the contour that seeds the segmentation process. The segment on the first post contrast image is defined by the two end points $S_{1-}$ and $S_{1+}$ that are located at equal distance d/2 around point p 212. The matched segment 224 on the second post contrast image is defined to be between points $S_{2-}$ and $S_{2+}$ that are set to be the closest points on contour 220 to points $S_{1-}$ and $S_{1+}$ or alternatively the cross points of the perpendicular lines from points $S_{1-}$ and $S_{1+}$ to contour 220. Similarly, points $S_{3-}$ and $S_{3+}$ are set based on points $S_{2-}$ and $S_{2+}$ to define contour 230.

Reference is now made back to FIG. 1. Step 160 refers to fitting the previously calculated displacements to an interstitial fluid flow model, and extracting for each segment, an estimation of the interstitial fluid velocity of the solid tumor.

Several models may be used. An exemplary model for the interstitial fluid velocity assumes that there is no interstitial fluid convection between the central tumor region and the tumor contour. At the tumor boundary, interstitial fluid flow velocity is maximum ($v=v_o$) and the interstitial fluid flow velocity declines linearly from the tumor surface into the surrounding normal tissue as a function of the distance from the tumor contour.

The velocity is described by the linear formula: $v(S)=v_o - bS$, and the displacement versus time function due to this model is described by: $S(t)=S_o*(1-e^{-bt})$ where b is a model attenuation coefficient and $S_o$ is the maximum displacement the contrast material can flow outwards from the tumor.

Figure 3:
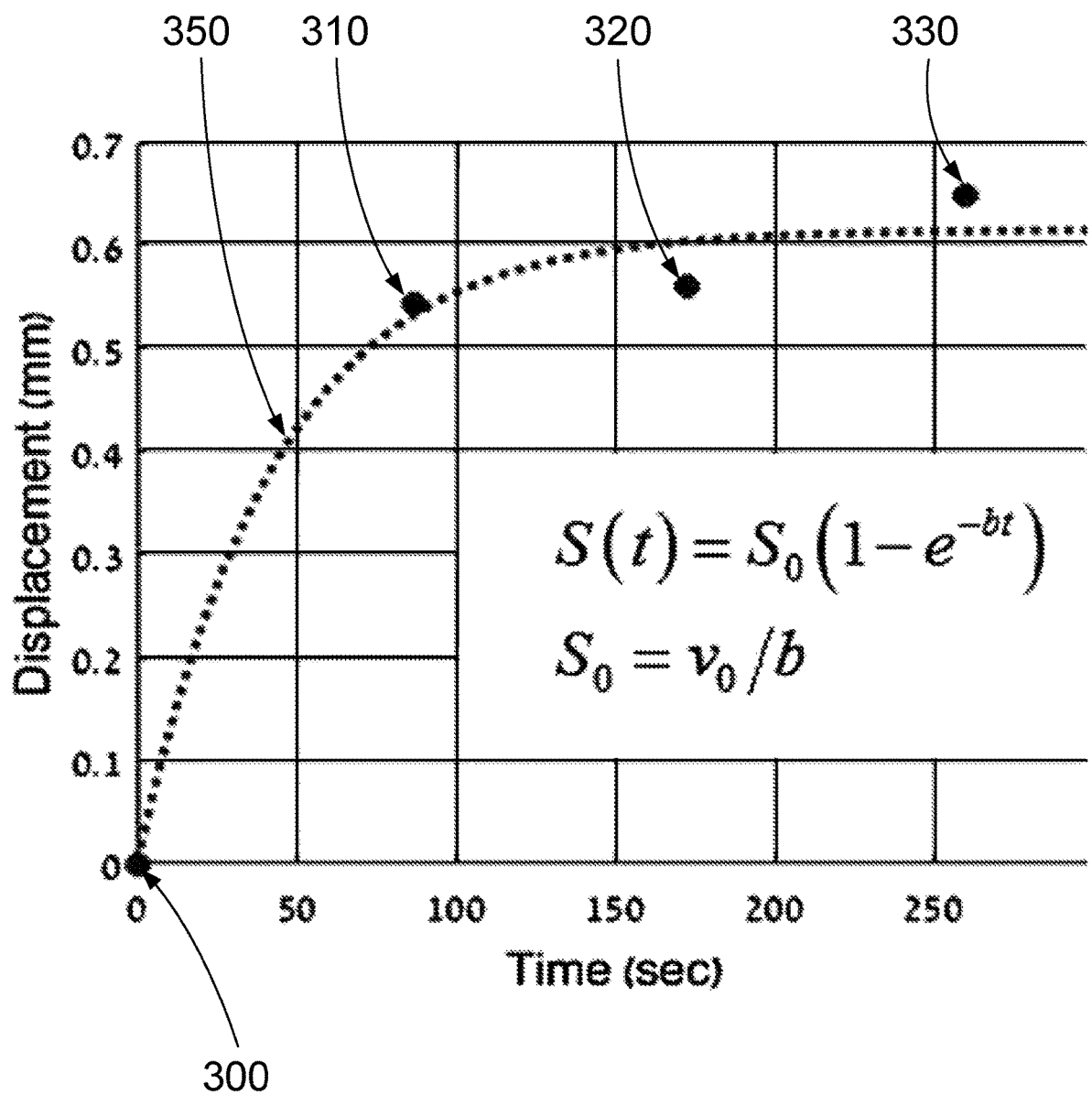
FIG. 3 illustrates fitting of the displacement measurements to the flow model.

Reference is now made to FIG. 3. FIG. 3 illustrates fitting of the displacement measurements to the flow model. Point 300 at time 0 refers to the first post-contrast image.

The second point 310 refers to the second post-contrast image. As can be seen in the illustration, the image was taken 90 second after the first post-contrast image, and the displacement of the illustrated segment was about 0.55 mm.

Points 320 and 330 refer to the displacement calculation of the third and fourth post-contrast images respectively. Dashed line 350 illustrates the best fit to the flow model equation.

Many fitting methods may be used. In an exemplary embodiment of the invention, a non-linear least squares regression analysis is used. The interstitial fluid flow velocity on the tumor perimeter, $v_o$, is extracted from this fit.

In case the data points do not fit the model well, the measurements taken from such non-fitting segments may be omitted. In an exemplary embodiment of the invention, only segments with fitting values of $R^2 > 0.7$ are considered for further analysis.

Reference is now made back to FIG. 1. Step 170 refers to calculating and reporting a characterization of the solid tumor comprises a direct assessment for at least the following measures: (a) the tumor and peri-tumor interstitial fluid velocity, (b) the attenuation coefficient of the interstitial fluid flow model (c) any combination or distribution of these measures or other parameters that are related to a flow model in general.

The above mentioned measures indirectly provide an assessment for the following indications: (a) the tumor interstitial fluid pressure, (b) the tumor drug delivery efficiency as a predictive factor or as an indication for a targeted intervention (c) the tumor prognostic or metastasis risk factor.

In an exemplary embodiment of the invention, the reporting step includes outputting a colored graphical map that indicates the interstitial fluid velocity on the contour of the tumor.

In an exemplary embodiment of the invention, preceding step 130, a radiologist roughly marks the tumor contour by indicating markers on one or more images taken by the medical imager. The markers can be made on any image taken at any time and on any slice or cross section. Typically the markers are made on a central largest slice in which the tumor seems clearly differentiated from the healthy surrounding tissue.

In an exemplary embodiment of the invention, the time difference elapsing between recordation of each image is constant. For example, the time difference between images may be 90 seconds. Alternatively, the time difference between images may be in the range of 1 second to 5 minutes.

Alternatively, time difference between images may vary. For example, the time difference in the first images in the sequence may be shorter than the time difference for the last images in the sequence.

In an exemplary embodiment of the invention, the pixels or voxels around the segment are arranged as a spatial-temporal data vector. The data vector is provided to an artificial neural network that is pre-trained to provide an estimation of the interstitial fluid velocity of the segment.

Additionally or alternatively, the artificial neural network may be pre-trained to provide an estimation for the interstitial fluid pressure, the tumor drug delivery efficiency, or the tumor metastasis risk factor or any other biomarker In an exemplary embodiment of the invention, the artificial neural network is trained by the data provided by the fitting model analysis. Additionally or optionally, the artificial neural network is trained by data validated offline.

In an exemplary embodiment of the invention, the artificial neural network estimation is used whenever the fitting does not fit the model well. Alternatively, an artificial neural network estimation may be used in all segments.

Yet in another embodiment the characterization is performed using both the data fitting the model, and the artificial neural network.

The instant invention is thus useful to assess and characterize the tumor interstitial fluid pressure, or the peritumoral interstitial fluid velocity, of solid tumors present in mammalian tissues. These characterizations aid the physician in determining the ideal treatment plan for the specific patient. The invention is not dependent on the imaging acquisition protocol, and thus is applicable as a routine diagnostic tool, useful in any medical setting, in contrast to prior art methods. The invention is automated, and does not require significant added effort from medical personnel or from the patient. The method is non-invasive, and as it uses standard images, does not require extraneous cost or effort from the patient or from the HMO provider.

Figure 4:
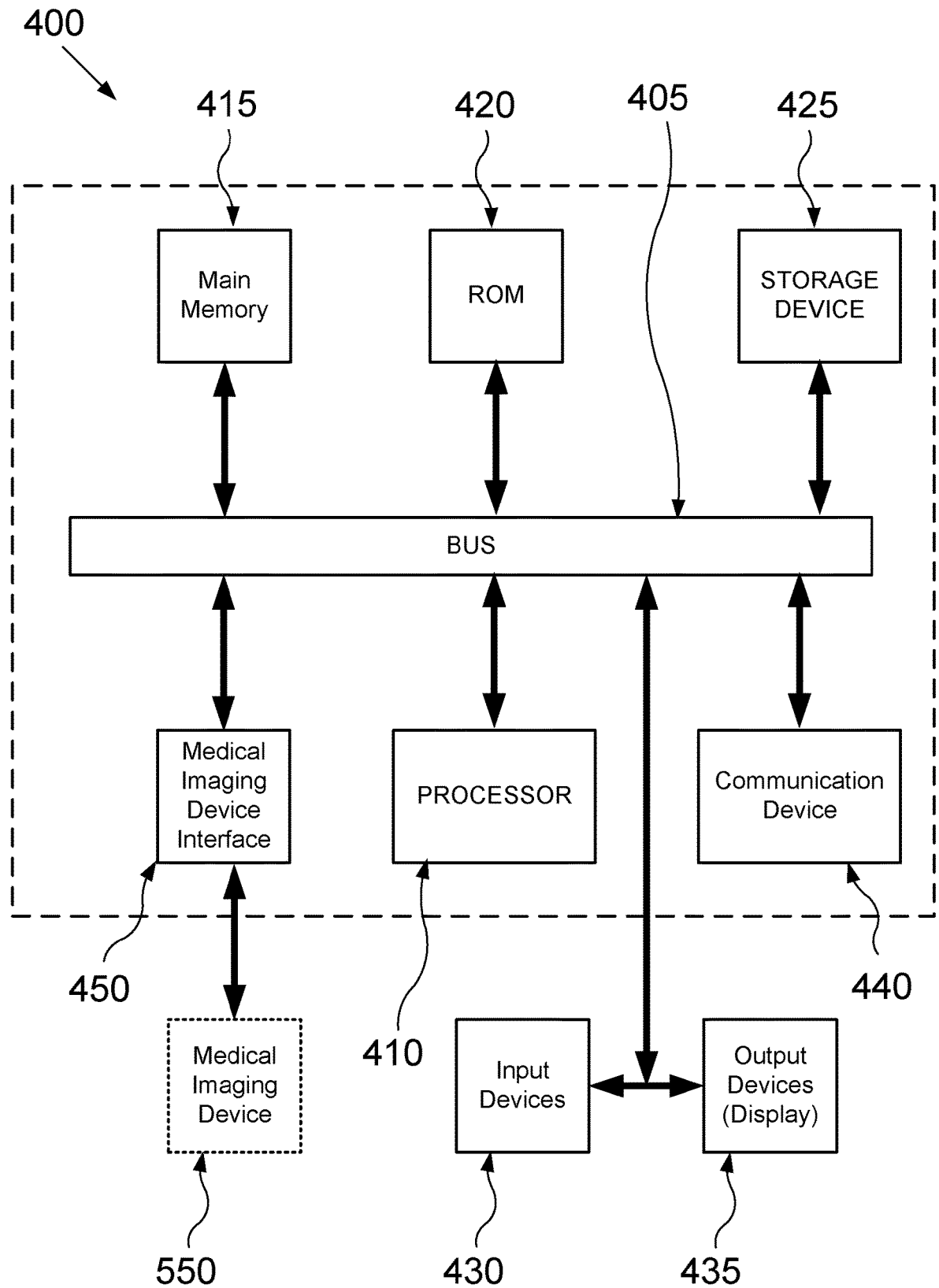
FIG. 4 illustrates an exemplary block diagram of a computing system for automated characterization of solid tumors, according to the invention.

Reference is now made to FIG. 4. FIG. 4 illustrates an exemplary block diagram of a computing system for automated characterization of solid tumors which may be used in accordance with an illustrative implementation of the current invention.

Computing system 400 includes a bus 405 or other communication component for communicating information and one or more processors 410 or processing circuits coupled to bus 405 for processing information. Computing system 400 also includes main memory 415, such as a random access memory (RAM) or other dynamic storage device, coupled to bus 405 for storing information, and instructions to be executed by processor 410. Main memory 415 may also be used for storing position information, temporary variables, or other intermediate information during execution of instructions by processor 410. Computing system 400 may further include a read-only memory (ROM) 420 or other static storage device coupled to bus 405 and configured to store static information and instructions for processor 410. A storage device 425, such as a solid state device, magnetic disk or optical disk, is coupled to bus 405 for persistently storing information and instructions.

Computing system 400 further includes an interface 450. Interface 450 is configured to acquire data from a medical imaging device 550. The acquired data (e.g. images) may be stored in main memory 415 and/or storage device 425 and processed by processor 410 in accordance to the methods described hereinabove.

Medical imaging device 550 may be a magnetic resonance imager (MRI). Alternatively, medical imaging device 550 may be an X-ray tomography imager.

In an exemplary embodiment of the invention, medical imaging device 550 is Positron emission tomography (PET), alternatively, medical imaging device 550 is Single-Photon Emission Computed Tomography (SPECT) or Ultrasound imager.

In an exemplary embodiment of the invention, medical imaging device 550 fuses several imaging technics, as mentioned above, to provide combined imaging data.

Computing system 400 may be coupled via bus 405 to an output device 435, output device 435 may be a display, such as a liquid crystal display, or active matrix display, for reporting the tumor assessments and displaying additional information to a user. An input device 430, such as a keyboard, may be coupled to bus 405 and configured to communicate information and command selections to processor 410. In another implementation, input device 430 may include a touch screen display, a cursor control, such as a mouse, a trackball, or cursor direction keys, and the like.

Computing system 400 may be coupled via bus 405 to one or more communication device 440, such as Ethernet, Wi-Fi, GSM or NFC communication device, for communication with additional devices and with a network, e.g. the Internet. Computing system 400 may use computing services, storage services or other services from the network.

According to various implementations, the processes described herein may be implemented by computing system 400 in response to the processor 410 executing an arrangement of instructions contained in main memory 415. Such instructions may be read into main memory 415 from another computer-readable medium, such as the storage device 425. Execution of the arrangement of instructions contained in main memory 415 causes computing system 400 to perform the illustrative processes described herein. One or more processors in a multi-processing arrangement may also be employed to execute the instructions contained in main memory 415. In alternative implementations, image processing accelerators and hard-wired circuitry may be used in place of or in combination with software instructions to effect illustrative implementations. Thus, implementations are not limited to any specific combination of hardware circuitry and software.

Although an example computing system has been described in FIG. 4, implementations described in this specification may be implemented in other types of digital electronic circuitry, or in computer software, firmware, or hardware. The computing system may be implemented on a server or on a plurality of identical servers, i.e., server farm and can be partially or entirely as a web service on the cloud.

EXAMPLE

A retrospective dataset of 12 breast cancer patients who underwent neoadjuvant therapy was utilized. These patients were subjected to Dynamic Contrast-enhanced (DCE)-MRI pre-treatment. MR images were acquired with a 1.5-T (Signa Excite HDX, GE Healthcare) device with a dedicated double breast coil (eight channels) and a standard dynamic bilateral breast MRI protocol. Dynamic contrast-enhanced T1-weighted images were acquired using a 3D axial vibrant multiphase with the following parameters: repetition time (TR)/echo time (TE)=5.4/2.6; flip angle, 15; bandwidth, 83.3 kHz; matrix, 512×512; FOV=340 mm; section thickness, 2 mm; no intersection gap. Subsequently, a bolus of contrast material (Dotarem®-gadoterate meglumine) was administered using an automated injector at 2 ml/sec, followed by a 20-ml saline flush at the same injection rate. The dose was adjusted to 0.1 ml/kg of body weight. Thereafter, five contrast-enhanced axial vibrant multiphase series were acquired. Time resolution between the images was 1.5 min. Finally, axial and sagittal fast spin-echo T2-weighted images with water suppression (TR/TE, 6000/80; slice thickness, 3 mm; matrix, 256×256; repetitions, 2; FOV, 16 cm) and sagittal T2-weighted sequences with fat suppression (3000/156; inversion time, 180 ms; echo-train length 16; slice thickness, 4 mm; matrix, 256×192; repetition, 1; FOV, 20 cm) were obtained separately for each breast. The central large slice of each tumor was digitally marked on the second subtraction by a breast radiologist. This contour served to initialize the automated segmentation algorithm.

It is expected that during the life of a patent maturing from this application many relevant processing will be developed.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the hereinabove example.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method for automated characterization of solid tumors in mammalian tissue, using medical imaging, the method comprising:
 (a) acquiring a sequence of images of mammalian tissue, captured with a medical imager using a Dynamic Contrast Enhanced (DCE) imaging protocol;
 (b) performing image registration of the sequence of images to align the sequence of images and compensate for at least one of the following: patient movements, respiration movement, and gravity effects;

(c) if a solid tumor is present, detecting a contour of said solid tumor in each one of said post; contrast images, among said sequence of images;

(d) dividing said contours to segments, and matching segments that are related to different images, in the sequence of images;

(e) calculating a displacement of the contrast material of the DCE protocol between each of said matched segments;

(f) fitting said displacements to a fluid flow model, and extracting for each segment, an estimation of the interstitial fluid velocity;

(g) conditioned upon one or more of said estimations of said interstitial fluid velocity of said segments, calculating and reporting a characterization of the solid tumor, wherein said characterization comprises an assessment for at least one of or any combination of:
the tumor or peri-tumor interstitial fluid velocity,
the tumor interstitial fluid pressure,
the tumor drug delivery efficiency, or
the tumor prognostic or metastasis risk,
wherein step (e) and step (f) further comprise preparing a spatial-temporal data vector of the segment, inputting said spatial-temporal data vector into an artificial neural network that is pre-trained to provide an estimation of the interstitial fluid velocity of the segment.

2. The method of claim 1, wherein in step (g) only a portion of the segment interstitial fluid velocity estimations are used in calculating said solid tumor characterization.

3. The method of claim 1, wherein step (f) further comprises extracting, for each segment, an estimation of an attenuation coefficient of the interstitial fluid flow model.

4. The method of claim 1, wherein in step (c) the contour is detected using a Distance Regularized Level Set Evolution (DRLSE) algorithm.

5. The method of claim 1, wherein step (c) comprises an initial contour guess, either manually marked by a radiologist, or automatically detected by at least one of or any combination of the following algorithms: (1) K-means, (2) Mean-shift, (3) Expectation-Maximization fitting, and (4) edge detection.

6. The method of claim 1, wherein step (c) further comprises smoothing the contour.

7. The method of claim 1, wherein calculating the displacement in step (e) is based on the Hausdorff distance between segments.

8. The method of claim 1, wherein fitting said displacements to a fluid flow model in step (f) is performed using a non-linear least squares regression analysis.

9. The method of claim 1, wherein the method further comprises providing maps of interstitial fluid velocities at the contour of said solid tumor.

10. The method of claim 1, wherein said medical imager is at least one of or any combination of: (a) X-ray tomography imager, (b) magnetic resonance imager (MRI), (c) Positron emission tomography (PET), (d) Single-photon emission computed tomography (SPECT), and (e) an ultrasound imager.

11. The method of claim 1, wherein said segments in step (d) are extracted from a single image slice, wherein the tumor is seen largest in this slice.

12. The method of claim 1, wherein said segments in step (d) are extracted from a plurality of image slices.

13. The method of claim 1, wherein said segments in step (d) are two-dimensional (2D) surfaces patches extracted from the images.

14. The method of claim 1, wherein steps (e) and step (f) are replaced with the steps of preparing a spatial-temporal data vector of the segment, and inputting said spatial-temporal data vector into an artificial neural network that is pre-trained to provide an estimation of the interstitial fluid velocity of the segment.

15. A non-transitory computer readable medium storing a program causing a computer to execute the method of characterization of solid tumors of claim 1.

16. A computing system for automated characterization of solid tumors, the computing system comprising:
i. an interface, wherein the interface is configured to acquire data from medical imaging system;
ii. one or more processors, wherein the processors are configured to perform the following:
(a) acquire a sequence of images from a medical imager using a Dynamic Contrast Enhanced (DCE) imaging protocol;
(b) perform image registration of the sequence of images to align the sequence of images and compensate for at least one of the following: patient movements, respiration movement, and gravity effects;
(c) if a solid tumor is present, detect a contour of said solid tumor in each one of said post contrast images, among said sequence of images;
(d) divide said contours to segments, and match segments that are related to different images, in the sequence of images;
(e) calculate a displacement of the contrast material of the DCE protocol between each of said matched segments;
(f) fit said displacements to a fluid flow model, and extract for each segment, an estimation of the interstitial fluid velocity;
(g) conditioned upon one or more of said estimations of said interstitial fluid velocity of said segments, calculate and report a characterization of the solid tumor, wherein said characterization comprises an assessment for at least one of or any combination of:
the tumor or peri-tumor interstitial fluid velocity,
the tumor interstitial fluid pressure,
the tumor drug delivery efficiency, or
the tumor prognostic or metastasis risk; and
iii. outputting device that reports the characterization of said solid tumor,
wherein step (e) and step (f) further comprise preparing a spatial-temporal data vector of the segment, inputting said spatial-temporal data vector into an artificial neural network that is pre-trained to provide an estimation of the interstitial fluid velocity of the segment.

17. The computing system of claim 16, wherein the acquired data is data from a magnetic resonance imager (MRI).

18. The computing system of claim 16, wherein the acquired data is data from an X-ray tomography imager.

19. The computing system of claim 16, wherein the acquired data is data from is at least one of or any combination of: (a) X-ray tomography imager, (b) magnetic resonance imager (MRI), (c) Positron emission tomography (PET), (d) Single-photon emission computed tomography (SPECT), and (e) Ultrasound imager.

* * * * *